(12) United States Patent
Kalnes et al.

(10) Patent No.: US 8,222,463 B2
(45) Date of Patent: *Jul. 17, 2012

(54) PROCESS FOR GENERATION OF POLYOLS FROM SACCHARIDE CONTAINING FEEDSTOCK

(75) Inventors: Tom N. Kalnes, LaGrange, IL (US); Joseph A. Kocal, Glenview, IL (US); John Q. Chen, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/193,072

(22) Filed: Jul. 28, 2011

(65) Prior Publication Data

US 2011/0312051 A1    Dec. 22, 2011

(51) Int. Cl.
*C07C 29/00* (2006.01)
*C07C 31/18* (2006.01)

(52) U.S. Cl. ........................ 568/852; 568/861

(58) Field of Classification Search .................. 568/861
See application file for complete search history.

(56) References Cited

U.S. PATENT DOCUMENTS

| | | | |
|---|---|---|---|
| 4,239,633 A | 12/1980 | Gutierrez et al. | |
| 5,227,356 A | 7/1993 | Hess et al. | |
| 5,616,304 A | 4/1997 | Stormo | |
| 6,162,350 A | 12/2000 | Soled et al. | |
| 6,436,279 B1 | 8/2002 | Colyar | |
| 6,447,645 B1 * | 9/2002 | Barrett et al. | 162/233 |
| 6,627,780 B2 | 9/2003 | Wu et al. | |
| 7,767,867 B2 | 8/2010 | Cortright | |
| 7,960,594 B2 * | 6/2011 | Zhang et al. | 568/861 |
| 2004/0175806 A1 | 9/2004 | Werpy et al. | |
| 2009/0130502 A1 | 5/2009 | Liu et al. | |
| 2010/0255983 A1 * | 10/2010 | Zhang | 502/178 |
| 2011/0046419 A1 | 2/2011 | Zhang et al. | |

FOREIGN PATENT DOCUMENTS

| | | |
|---|---|---|
| WO | 2006/092085 A1 | 9/2006 |
| WO | 2010/045766 A1 | 4/2010 |
| WO | 2010/060345 A1 | 6/2010 |
| WO | 2011/113281 A1 | 9/2011 |

OTHER PUBLICATIONS

Ji et al. Catalytic conversion of cellulose into ethylene glycol over supported carbide catalysts. Catalysis Today, 2009, vol. 147, 77-85.*
Ji et al. Direct Conversion of Cellulose into Ethylene Glycol Using Nickel-Promoted Tungsten Carbide Catalysts. Angew. Chem. Int. Ed., 2008, vol. 47, 8510-8513.*
Ji, "Catalytic conversion of cellulose into ethylene glycol over supported carbide catalysts", Catalysis Today, 2009, pp. 75-85, vol. 147, Issue 2.
Ji, "Direct Catalytic Conversion of Cellulose into Ethylene Glycol Using Nickel-Promoted Tungsten Carbide Catalysts", Angew. Chem. Int. Ed, 2008, pp. 8510-8513, vol. 47, Issue 44.
Zhang, "A new 3D mesoporous carbon replicated from commercial silica as a catalyst support for direct conversion of cellulose into ethylene glycol", Chem. Commun., 2010, pp. 862-864, vol. 46, Issue 6.
Zhang, "Hydrolysis of cellulose into glucose over carbons sulfonated at elevated temperatures", Chem Commun., 2010, pp. 6935-6937, vol. 46, Issue 37.
Zhang, "Catalytic Hydrogenation of Corn Stalk to Ethylene Glycol and 1,2-Propylene Glycol", Ind. End. Chem, Res., 2011,pp. 6601-6608, vol. 50, Issue 11.
Zhang, "Transition Metal—Tungsten Bimetallic Catalysts for the Conversion of Cellulose into Ethylene Glycol", ChemSusChem, 2010, pp. 63-66, vol. 50, Issue 11.
Jin, "Effect of Ni Promoter on Dibenzothiophene Hydrodesulfurization Performance of Molybdenum Carbide Catalyst", Chinese Jour. of Catalysis, 2006, pp. 899-903, vol. 27, Issue 10.
Narayan, "Ethylene Glycol and Other monomeric Polyols from Biomass", Biotechnology and Bioengineering Symposium, No. 14, 1984, pp. 563-571.
Zhou, "One-pot Conversion of Jerusalem Artichoke Tubers into Polyols", 7th Asia Pacific Conference on Sustainable Energy and Environmental Technologies, Oct. 15-17, 2009.
China Explores in Manufacture of Ethylene Glycol from Renewable Resources', China Petroleum processing and Petrochemical Technology, No. 1, 2009, p. 44.
Zheng, "Direct Catalytic Conversion Cellulose into Ethylene Glycol", 8th World Congress of Chemical Engineering, 2009, p. 512e.
U.S. Office action dated Dec. 9, 2011 for U.S. Appl. No. 13/192,739, Zhang et al.
U.S. Office action dated Dec. 14, 2011 for U.S. Appl. No. 13/192,835, Kalnes et al.
U.S. Office action dated Dec. 14, 2011 for U.S. Appl. No. 13/193,200, Kalnes et al.
U.S. Office action dated Dec. 15, 2011 for U.S. Appl. No. 13/193,227, Kalnes et al.
U.S. Office action dated Dec. 9, 2011 for U.S. Appl. No. 13/192,907, Chen et al.
U.S. Office action dated Dec. 14, 2011 for U.S. Appl. No. 13/192,970, Kalnes et al.
U.S. Office action dated Dec. 15, 2011 for U.S. Appl. No. 13/193,007, Chen et al.
Applicant's Mar. 9, 2012 response to the Dec. 9, 2011 Office Action for U.S. Appl. No. 13/192,739, Zhang et al.
Applicant's Mar. 14, 2012 response to the Dec. 14, 2011 Office Action for U.S. Appl. No. 13/192,835, Kalnes et al.
Applicant's Mar. 12, 2012 response to the Dec. 14, 2011 Office Action for U.S. Appl. No. 13/193,200, Kalnes et al.
Applicant's Mar. 12, 2012 response to the Dec. 15, 2011 Office Action for U.S. Appl. No. 13/193,227, Kalnes et al.

(Continued)

Primary Examiner — Sikarl Witherspoon
(74) Attorney, Agent, or Firm — Maryann Maas (57) ABSTRACT

A process for generating at least one polyol from a feedstock comprising saccharide is performed in a continuous or batch manner. The process involves, contacting hydrogen, water, and a feedstock comprising saccharide, with a catalyst system to generate an effluent stream comprising at least one polyol and recovering the polyol from the effluent stream. The catalyst system comprises at least one metal component with an oxidation state greater than or equal to 2+.

20 Claims, 2 Drawing Sheets

OTHER PUBLICATIONS

Applicant's Mar. 9, 2012 response to the Dec. 9, 2011 Office Action for U.S. Appl. No. 13/192,907, Chen et al.

Applicant's Mar. 12, 2012 response to the Dec. 14, 2011 Office Action for U.S. Appl. No. 13/192,970, Kalnes et al.

Applicant's Mar. 12, 2012 response to the Dec. 15, 2011 Office Action for U.S. Appl. No. 13/193,007, Chen et al.

* cited by examiner

PROCESS FOR GENERATION OF POLYOLS FROM SACCHARIDE CONTAINING FEEDSTOCK

FIELD OF THE INVENTION

The invention relates to a process for generating at least one polyol from a feedstock comprising at least one saccharide using a specific catalyst system. The process involves, contacting hydrogen, water, and the feedstock comprising saccharide, with a catalyst system to generate an effluent comprising at least one polyol and recovering the polyol from the effluent. The catalyst system comprises both a metal component with an oxidation state greater than or equal to 2+ and a hydrogenation component.

BACKGROUND OF THE INVENTION

Polyols are valuable materials that find use in the manufacture of cold weather fluids, cosmetics, polyesters and many other synthetic products. Generating polyols from saccharides instead of fossil fuel-derived olefins can be a more environmentally friendly and a more economically attractive process. Previously, polyols have been generated from polyhydroxy compounds, see WO 2006/092085 and US 2004/0175806. Recently, catalytic conversion of saccharide into ethylene glycol over supported carbide catalysts was disclosed in Catalysis Today, 147, (2009) 77-85. US 2010/0256424, US 2010/0255983, and WO 2010/060345 teach a method of preparing ethylene glycol from saccharide and a tungsten carbide catalyst to catalyze the reaction. Tungsten carbide catalysts have also been published as successful for batch-mode direct catalytic conversion of saccharide to ethylene glycol in Angew. Chem. Int. Ed 2008, 47, 8510-8513 and supporting information. A small amount of nickel was added to a tungsten carbide catalyst in Chem. Comm. 2010, 46, 862-864. Bimetallic catalysts have been disclosed in ChemSusChem, 2010, 3, 63-66. Additional references disclosing catalysts known in the art for the direct conversion of cellulose to ethylene glycol or propylene glycol include WO2010/060345; U.S. Pat. No. 7,767,867; Chem. Commun., 2010, 46, 6935-6937; Chin. J. Catal., 2006, 27(10): 899-903; and Apcseet UPC 2009 7$^{th}$ Asia Pacific Congress on Sustainable Energy and Environmental Technologies, "One-pot Conversion of Jerusalem Artichoke Tubers into Polyols.

However, there remains a need for new catalyst systems effective for direct conversion of saccharide to polyol, and especially for catalyst systems that may be better suited for larger scale production or commercial production facilities. The process and catalyst system comprising at least one metal component (M1) selected from IUPAC Group 4, 5 or 6 of the periodic table with an oxidation state greater than or equal to 2+ and at least one hydrogenation component (M2) selected from IUPAC Group 8, 9, or 10 of the periodic table for generating at least one polyol from a feedstock comprising at least one saccharide described herein addresses this need. The metal component (M1) is in a form other than a carbide, nitride or phosphide.

SUMMARY OF THE INVENTION

The invention employs a catalyst system useful for the conversion of at least one saccharide to polyol, the catalyst system comprising a metal component with an oxidation state greater than or equal to 2+ (M1) and a hydrogenation component (M2). The metal component M1 is selected from IUPAC Groups 4, 5 and 6 of the Periodic table, and the hydrogenation component (M2) is selected from the group consisting of IUPAC Groups 8, 9, and 10 of the Periodic Table. The metal component (M1) may be selected from the group consisting of tungsten, molybdenum, vanadium, niobium, chromium, titanium, zirconium and any combination thereof. The metal component may be comprised within a compound. The metal component is in a form other than a carbide, nitride, or phosphide The hydrogenation component may comprise, for example, an active metal component selected from the group comprising Pt, Pd, Ru, Rh, Ni, Ir, and combinations thereof. M1, M2 or both M1 and M2 may be unsupported or supported on a solid catalyst support. The solid catalyst support is selected from the group consisting of carbon, $Al_2O_3$, $ZrO_2$, $SiO_2$, MgO, $Ce_xZrO_y$, $TiO_2$, SiC, silica alumina, zeolites, clays and combinations thereof. The mass ratio of M1 to M2, on an elemental basis, ranges from about 1:100 to about 100:1. If supported, the M1 component, M2 component, or both the M1 and M2 components comprises from about 0.05 to about 30 mass percent, on an elemental basis of the supported catalyst. Measurements of the metal component and the hydrogenation component such as mass ratios, weight ratios, and mass percents are provided herein on an elemental basis with respect to the IUPAC Groups 4, 5 and 6 and IUPAC Groups 8, 9, and 10 elements of the Periodic Table.

One embodiment of the invention is a process for generating at least one polyol from a feedstock comprising at least one saccharide where the process comprises contacting hydrogen, water, and feedstock with a catalyst system to generate an effluent comprising at least one polyol, and recovering the polyol from the effluent. The process may be operated in a batch mode operation or in a continuous mode operation. The catalyst system comprises a metal component (M1) having an oxidation state greater than or equal to 2+ and a hydrogenation component (M2). The metal component M1 is selected from IUPAC Groups 4, 5 and 6 of the Periodic table, and the hydrogenation component (M2) is selected from the group consisting of IUPAC Groups 8, 9, and 10 of the Periodic Table. The metal component (M1) may be selected from the group consisting of tungsten, molybdenum, vanadium, niobium, chromium, titanium, zirconium and any combination thereof. The metal component may be comprised within a compound. The metal component is in a form other than a carbide, nitride, or phosphide The hydrogenation component may comprise an active metal component selected from the group comprising Pt, Pd, Ru, Rh, Ni, Ir, and combinations thereof. The hydrogenation component may be comprised within a compound. M2 or both M1 and M2 may be unsupported or supported on a solid catalyst support. The solid catalyst support is selected from the group consisting of carbon, $Al_2O_3$, $ZrO_2$, $SiO_2$, MgO, $Ce_xZrO_y$, $TiO_2$, SiC, silica alumina, zeolites, clays and combinations thereof. The mass ratio of M1 to M2 ranges from about 1:100 to about 100:1. If supported, the M1 component, M2 component, or both the M1 and M2 components comprises from about 0.05 to about 30 mass percent, on an elemental basis, of the supported catalyst.

Yet another embodiment of the invention is a continuous process for generating at least one polyol from a feedstock comprising at least one saccharide. The process involves, contacting, in a continuous manner, hydrogen, water, and a feedstock comprising at least one saccharide, with a catalyst system to generate an effluent stream comprising at least one polyol and recovering the polyol from the effluent stream. The hydrogen, water, and feedstock, are fed to the reactor in a continuous manner. The effluent stream is removed from the reactor in a continuous manner. The process is a catalytic process employing a catalyst system comprising a metal component (M1) having an oxidation state greater than or equal to 2+ and a hydrogenation component (M2) as described above.

In one embodiment, the contacting occurs in a reaction zone having at least a first input stream and a second input stream, the first input stream comprising at least the feedstock comprising at least one saccharide and the second input stream comprising hydrogen. The first input stream may be pressurized prior to the reaction zone and the second input stream may be pressurized and heated prior to the reaction zone. The first input stream may be pressurized and heated to a temperature below the thermal decomposition temperature of the saccharide prior to the reaction zone and the second input stream may be pressurized and heated prior to the reaction zone. The first input stream and the second input stream further comprise water.

In another embodiment of the invention, the polyol produced is at least ethylene glycol or propylene glycol. Co-products such as alcohols, organic acids, aldehydes, monosaccharides, disaccharides, oligosaccharides, polysaccharides, phenolic compounds, hydrocarbons, glycerol, depolymerized lignin, and proteins may also be generated. In one embodiment, the feedstock may be treated prior to contacting with the catalyst by a technique such as sizing, drying, grinding, hot water treatment, steam treatment, hydrolysis, pyrolysis, thermal treatment, chemical treatment, biological treatment, catalytic treatment, or combinations thereof.

The effluent stream from the reactor system may further comprise catalyst which may be separated from the effluent stream using a technique such as direct filtration, settling followed by filtration, hydrocyclone, fractionation, centrifugation, the use of flocculants, precipitation, liquid extraction, adsorption, evaporation, and combinations thereof.

DETAILED DESCRIPTION OF THE INVENTION

The invention involves a catalyst system and a process for generating at least one polyol from a feedstock comprising at least one saccharide. The catalyst system comprises metal component (M1) with an oxidation state greater than or equal to 2+ and a hydrogenation component (M2). The metal component (M1) is selected from IUPAC Groups 4, 5 and 6 of the Periodic table. In a specific embodiment, the metal component (M1) may be selected from the group consisting of tungsten, molybdenum, vanadium, niobium, chromium, titanium, zirconium and any combination thereof. The metal component may be comprised within a compound. The metal component is not in the form of a carbide, nitride, or phosphide. The hydrogenation component (M2) is selected from the group consisting of IUPAC Groups 8, 9, and 10 of the Periodic Table. The hydrogenation component may be comprised within a compound. In a specific embodiment, the hydrogenation component may comprise an active metal component selected from the group comprising Pt, Pd, Ru, Rh, Ni, Ir, and combinations thereof. M1, M2 or both M1 and M2 may be unsupported or supported on a solid catalyst support. The solid catalyst support is selected from the group consisting of carbon, $Al_2O_3$, $ZrO_2$, $SiO_2$, $MgO$, $Ce_xZrO_y$, $TiO_2$, $SiC$, silica alumina, zeolites, clays and combinations thereof. The mass ratio of M1 to M2 ranges from about 1:100 to about 100:1 on an elemental basis. If supported, the M1 component, M2 component, or both the M1 and M2 components comprises from about 0.05 to about 30 mass percent, on an elemental basis, of the supported catalyst. Measurements of the metal component and the hydrogenation component such as mass ratios, weight ratios, and mass percents are provided herein on an elemental basis with respect to the IUPAC Groups 4, 5 and 6 and IUPAC Groups 8, 9, and 10 elements of the Periodic Table.

The process involves contacting, hydrogen, water, and a feedstock comprising at least one saccharide, with the catalyst system described above to generate an effluent comprising at least one polyol, and recovering the polyol from the effluent. The process may be operated in a batch mode operation or in a continuous mode operation. When operated in a continuous mode, the process involves continuous catalytic conversion of a flowing stream of feedstock comprising saccharide to ethylene glycol or propylene glycol with high yield and high selectivity.

The feedstock comprises at least one saccharide which may be any class of monosaccharides, disaccharides, oligosaccharides, and polysaccharides and may be edible, inedible, amorphous or crystalline in nature. In one embodiment, the feedstock comprises polysaccharides that consist of one or a number of monosaccharides joined by glycosidic bonds. Examples of polysaccharides include glycogen, cellulose, hemicellulose, starch, chitin and combinations thereof. The term "saccharide" as used herein is meant to include all the above described classes of saccharides including polysaccharides.

In the embodiment where the saccharide is cellulose, hemicellulose, or a combination thereof, additional advantages may be realized. Hemicellulose is generally understood to be any of several polysaccharides that are more complex than a sugar. Economic conversion of cellulose and hemicellulose to useful products can be a sustainable process that reduces fossil energy consumption and does not directly compete with the human food supply. Cellulose and hemicellulose are large renewable resources having a variety of attractive sources, such as residue from agricultural production or waste from forestry or forest products. Since cellulose and hemicellulose cannot be digested by humans, using cellulose and or hemicellulose as a feedstock does not take from our food supply. Furthermore, cellulose and hemicellulose can be a low cost waste type feedstock material which is converted herein to high value products like polyols such as ethylene glycol and propylene glycol.

The feedstock comprising saccharide of the process may be derived from sources such as agricultural crops, forest biomass, waste material, recycled material. Examples include short rotation forestry, industrial wood waste, forest residue, agricultural residue, energy crops, industrial wastewater, municipal wastewater, paper, cardboard, fabrics, pulp derived from biomass, corn starch, sugarcane, grain, sugar beet, glycogen and other molecules comprising the molecular unit structure of $C_m(H_2O)_n$, and combinations thereof. Multiple materials may be used as co-feedstocks. With respect to biomass, the feedstock may be whole biomass including cellulose, lignin and hemicellulose or treated biomass where the polysaccharide is at least partially depolymerized, or where the lignin, hemicellulose or both have been at least partially removed from the whole biomass.

Depending upon the catalyst selection, the feedstock may be continuously contacted with the catalyst system in a reactor system such as an ebullating catalyst bed reactor system, an immobilized catalyst reactor system having catalyst channels, an augured reactor system, fluidized bed reactor systems, mechanically mixed reactor systems, slurry reactor systems, also known as a three phase bubble column reactor systems, and combinations thereof. Examples of operating conditions in the rector system include temperatures ranging from about 100° C. to about 350° C. and hydrogen pressures greater than about 150 psig. In one embodiment, the temperature in the reactor system may range from about 150° C. to about 350° C., in another embodiment the temperature in the reactor system may range from about 200° C. to about 280° C. The feedstock, which comprises at least one saccharide, may be continuously contacted with the catalyst system in the reactor system at a water to feedstock weight ratio ranging from about 1 to about 100, a catalyst (M1+M2) to feedstock weight ratio of greater than about 0.005, a pH of less than about 10 and a residence time of greater than five minutes. In another embodiment, the catalyst to feedstock weight ratio is greater than about 0.01.

The process of the invention may be operated in a batch mode operation, or may be operated in a continuous mode of operations. In a batch mode operation, the necessary reactants and catalyst system are combined and allowed to react. After a period of time, the reaction mixture is removed from the reactor and separated to recover products. Autoclave reactions are common examples of batch reactions. While the process may be operated in the batch mode, there are advantages to operating in the continuous mode, especially in larger scale operations. The following description will focus on continuous mode operation, although the focus of the following description does not limit the scope of the invention.

Unlike batch system operations, in a continuous process, the feedstock is continually being introduced into the reaction zone as a flowing stream and a product comprising a polyol is being continuously withdrawn. Materials must be capable of being transported from a low pressure source into the reaction zone, and products must be capable of being transported from the reaction zone to the product recovery zone. Depending upon the mode of operation, residual solids, if any, must be capable of being removed from the reaction zone.

A challenge in processing a feedstock comprising saccharide in a pressurized hydrogen environment is that the feedstock may be an insoluble solid. Therefore, pretreatment of the feedstock may be performed in order to facilitate the continuous transporting of the feedstock. Suitable pretreatment operations may include sizing, drying, grinding, hot water treatment, steam treatment, hydrolysis, pyrolysis, thermal treatment, chemical treatment, biological treatment, catalytic treatment, and combinations thereof. Sizing, grinding or drying may result in solid particles of a size that may be flowed or moved through a continuous process using a liquid or gas flow, or mechanical means. An example of a chemical treatment is mild acid hydrolysis of polysaccharide. Examples of catalytic treatments are catalytic hydrolysis of polysaccharide, catalytic hydrogenation of polysaccharide, or both, and an example of biological treatment is enzymatic hydrolysis of polysaccharide. Hot water treatment, steam treatment, thermal treatment, chemical treatment, biological treatment, or catalytic treatment may result in lower molecular weight saccharides and depolymerized lignins that are more easily transported as compared to the untreated polysaccharide. Suitable pretreatment techniques are found in "Catalytic Hydrogenation of Corn Stalk to Ethylene Glycol and 1,2-Propylene Glycol" Jifeng Pang, Mingyuan Zheng, Aiqin Wang, and Tao Zhang Ind. Eng. Chem. Res. DOI: 10.1021/ie102505y, Publication Date (Web): Apr. 20, 2011. See also, US 2002/0059991.

Another challenge in processing a feedstock comprising saccharide is that the saccharide is thermally sensitive. Exposure to excessive heating prior to contacting with the catalyst may result in undesired thermal reactions of the saccharide such as charring of the saccharide. In one embodiment of the invention, the feedstock comprising saccharide is provided to the reaction zone containing the catalyst in a separate input stream from the primary hydrogen stream. In this embodiment, the reaction zone has at least two input streams. The first input stream comprises at least the feedstock comprising saccharide, and the second input stream comprises at least hydrogen. Water may be present in the first input stream, the second input stream or in both input streams. Some hydrogen may also be present in the first input stream with the feedstock comprising saccharide. By separating the feedstock comprising saccharide and the hydrogen into two independent input streams, the hydrogen stream may be heated in excess of the reaction temperature without also heating the feedstock comprising saccharide to reaction temperature. The temperature of first input stream comprising at least the feedstock comprising saccharide may be controlled not to exceed the temperature of unwanted thermal side reactions. For example, the temperature of first input stream comprising at least the feedstock comprising saccharide may be controlled not to exceed the decomposition temperature of the saccharide or the charring temperature of the saccharide. The first input stream, the second input stream, or both may be pressurized to reaction pressure before being introduced to the reaction zone.

In the continuous processing embodiment, the feedstock comprising saccharide, after any pretreatment, is continuously introduced to a catalytic reaction zone as a flowing stream. Water and hydrogen, both reactants, are present in the reaction zone. As discussed above and depending upon the specific embodiment, at least a portion of the hydrogen may be introduced separately and independent from the feedstock comprising saccharide, or any combination of reactants, including feedstock comprising saccharide, may be combined and introduced to the reaction zone together. Because of the mixed phases likely to be present in the reaction zone specific types of reactor systems are preferred. For example, suitable reactor systems include ebullating catalyst bed reactor systems, immobilized catalyst reactor systems having catalyst channels, augured reactor systems, fluidized bed reactor systems, mechanically mixed reactor systems and slurry reactor systems, also known as a three phase bubble column reactor systems, and combinations thereof.

Furthermore, metallurgy of the reactor system is selected to be compatible with the reactants and the desired products within the range of operating conditions. Examples of suitable metallurgy for the reactor system include titanium, zirconium, stainless steel, carbon steel having hydrogen embrittlement resistant coating, carbon steel having corrosion resistant coating. In one embodiment, the metallurgy of the reaction system includes either coated or clad carbon steel.

Within the reaction zone and at operating conditions, the reactants proceed through catalytic conversion reactions to produce at least one polyol. Desired polyols include ethylene glycol and propylene glycol. Co-products may also be produced and include compounds such as alcohols, organic acids, aldehydes, monosaccharides, polysaccharides, phenolic compounds, hydrocarbons, glycerol, depolymerized lignin and proteins. The co-products may have value and may be recovered in addition to the product polyols. The reactions may proceed to completion, or some reactants and intermediates may remain in a mixture with the products. Intermediates, which are included herein as part of the co-products, may include compounds such as depolymerized cellulose, lignin and hemicellulose. Unreacted hydrogen, water, and polysaccharide may also be present in the reaction zone effluent along with products and co-products. Unreacted material and or intermediates may be recovered and recycled to the reaction zone.

The reactions are catalytic reactions and the reaction zone comprises at least one catalyst system where the catalyst system comprises a metal component with an oxidation state greater than or equal to 2+ (M1) and a hydrogenation component (M2). The metal component M1 is selected from IUPAC Groups 4, 5 and 6 of the Periodic table, and the hydrogenation component (M2) is selected from the group consisting of IUPAC Groups 8, 9, and 10 of the Periodic Table. The catalyst system may also be considered a multi-component catalyst, and the terms are used herein interchangeably.

The metal component (M1) may be present in the catalyst system in any catalytically available form that has the metal component in an oxidation state greater than or equal to 2+. The metal component may be in a compound or may be in chemical combination with one or more of the other ingredients of the catalyst system. For example, the metal component (M1) may be selected from the group consisting of tungsten, molybdenum, vanadium, niobium, chromium, titanium, zirconium and any combination thereof. The metal component may be comprised within a compound. The metal component is in a form other than a carbide, nitride, or phosphide. Compounds comprising the M1 component of the catalyst system may be selected from the group consisting of tungstic acid, molybedic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. The hydrogenation component (M2) may be present in the catalyst system in any catalytically available form. The hydrogenation component may in the elemental form or may be a compound or may be in chemical combination with one or more of the other ingredients of the catalyst system. For example, the hydrogenation component may comprise an active metal component selected from the group comprising Pt, Pd, Ru, Rh, Ni, Ir, and combinations thereof.

The metal component M1, the hydrogenation component M2 or both M1 and M2 may be unsupported or supported on one or more solid catalyst supports. Refractory oxide catalyst supports and others may be used. The mass ratio of M1 to M2, on an elemental basis, ranges from about 1:100 to about 100:1. If supported, the M1 component, M2 component, or both the M1 and M2 components comprises from about 0.05 to about 30 mass percent, on an elemental basis, of the supported catalyst. The description below generally refers to the catalyst support. Such general description to the catalyst support is not meant to limit the broad scope of the invention to a single catalyst support. For example in one embodiment M1 is supported on a first catalyst support and M2 is supported on a second catalyst support and the first catalyst support and the second catalyst support may be the same composition or different compositions.

The support may be in the shape of a powder, or specific shapes such as spheres, extrudates, pills, pellets, tablets, irregularly shaped particles, monolithic structures, catalytically coated tubes, or catalytically coated heat exchanger surfaces. Examples of the refractory inorganic oxide supports include but are not limited to silica, aluminas, silica-alumina, titania, zirconia, magnesia, clays, zeolites, molecular sieves, etc. It should be pointed out that silica-alumina is not a mixture of silica and alumina but means an acidic and amorphous material that has been cogelled or coprecipitated. Carbon and activated carbon may also be employed as supports. Specific suitable supports include carbon, activated carbon, $Al_2O_3$, $ZrO_2$, $SiO_2$, MgO, $Ce_xZrO_y$, $TiO_2$, SiC, silica alumina, zeolites, clays and combinations thereof. Of course, combinations of materials can be used as the support. M1, M2, or the combination of M1 and M2 may be incorporated onto the catalytic support in any suitable manner known in the art, such as by coprecipitation, coextrusion with the support, or impregnation. M1, M2, or the combination of M1 and M2 may comprise from about 0.05 to about 30 mass %, on an elemental basis, of the supported catalyst. In another embodiment, M1, M2, or the combination of M1 and M2 may comprise from about 0.3 to about 15 mass %, on an elemental basis, of the supported catalyst. In still another embodiment, M1, M2, or the combination of M1 and M2 may comprise from about 0.5 to about 7 mass %, on an elemental basis, of the supported catalyst.

The relative amount of M1 catalyst component to M2 catalyst component may range from about 1:100 to about 100:1 as measured by ICP or other common wet chemical analysis methods. In another embodiment, the relative amount of M1 catalyst component to M2 catalyst component may range from about 1:20 to about 50:1, and in still another embodiment, the relative amount of M1 catalyst component to M2 catalyst component may range from about 1:10 to about 10:1.

The amount of the catalyst system used in the process may range from about 0.005 to about 0.4 mass % of the feedstock comprising saccharide. In other embodiment, the amount of the catalyst system used in the process may range from about 0.01 to about 0.25 mass % of the feedstock comprising saccharide. In still other embodiment, the amount of the catalyst system used in the process may range from about 0.02 to about 0.15 mass % of the feedstock comprising saccharide. The reactions occurring are multistep reactions and different amounts of the catalyst system, or relative amounts of the components of the catalyst system, can be used to control the rates of the different reactions. Individual applications may have differing requirements as to the amounts of the catalyst system, or relative amounts of the components of the catalyst system used.

In one embodiment of the invention, the M1 catalyst component may be a solid that is soluble in the reaction mixture, or at least partially soluble in the reaction mixture which includes at least water and the feedstock at reaction conditions. An effective amount of the solid M1 catalyst should be soluble in the reaction mixture. Different applications and M1 catalyst components will result in differing effective amounts of M1 catalyst component needed to be in solution in the reaction mixture. In another embodiment of the invention, the M1 catalyst component is miscible or at least partially miscible with the reaction mixture. As with the solid M1 catalyst component, an effective amount of the liquid M1 catalyst should be miscible in the reaction mixture. Again, different applications and different M1 catalyst components will result in differing effective amounts of M1 catalyst component needed to be miscible in the reaction mixture. Typically, the amount of M1 catalyst component miscible in water is in the range of about 1 to about 100%, in another embodiment, from about 10 to about 100%, and in still another embodiment, from about 20 to about 100%.

The multicomponent catalyst of the present invention may provide several advantages over a more traditional single component catalyst. For example, in some embodiments, the manufacture costs of the catalyst may be reduced since fewer active components need to be incorporated onto a solid catalyst support. Operational costs may be reduced since it is envisioned that less catalyst make-up will be required and more selective processing steps can be used for recovery and recycle of catalyst. Other advantages include improved catalyst stability which leads to lower catalyst consumption and lower cost per unit of polyol product, and the potential for improved selectivity to ethylene glycol and propylene glycol with reduced production of co-boiling impurities such as butane diols.

In some embodiments the catalyst system may be contained within the reaction zone, and in other embodiments the catalyst may continuously or intermittently pass through the reaction zone, and in still other embodiments, the catalyst system may do both, with at least one catalyst system component residing in a reaction zone while the other catalyst system component continuously or intermittently passes through the reaction zone. Suitable reactor systems include an ebullating catalyst bed reactor system, an immobilized catalyst reactor system having catalyst channels, an augured reactor system, a fluidized bed reactor system, a mechanically mixed reactor systems, a slurry reactor system, also known as a three phase bubble column reactor system and combinations thereof.

Examples of operating conditions in the rector system include temperatures ranging from about 100° C. to about 350° C. and hydrogen pressures greater than about 150 psig. In one embodiment, the temperature in the reactor system may range from about 150° C. to about 350° C., in another embodiment the temperature in the reactor system may range from about 200° C. to about 280° C. The feedstock, which comprises at least one saccharide, may be continuously contacted with the catalyst system in the reactor system at a water to feedstock weight ratio ranging from about 1 to about 100, a catalyst (M1+M2) to feedstock weight ratio of greater than about 0.005, a pH of less than about 10 and a residence time of greater than 5 minutes. In another embodiment, the water to feedstock weight ratio ranges from about 1 to about 20 and the catalyst to feedstock weight ratio is greater than about 0.01. In yet another embodiment, the water to feedstock weight ratio ranges from about 1 to about 5 and the catalyst to feedstock weight ratio is greater than about 0.1.

In one embodiment of the invention, the catalytic reaction system employs a slurry reactor. Slurry reactors are also known as three phase bubble column reactors. Slurry reactor systems are known in the art and an example of a slurry reactor system is described in U.S. Pat. No. 5,616,304 and in Topical Report, Slurry Reactor Design Studies, DOE Project No. DE-AC22-89PC89867, Reactor Cost Comparisons, which may be found at http://www.fischer-tropsch.org/DOE/DOE_reports/91005752/de91005752_toc.htm. The catalyst system may be mixed with the water and feedstock comprising saccharide to form a slurry which is conducted to the slurry reactor. The reactions occur within the slurry reactor and the catalyst is transported with the effluent stream out of the reactor system. The slurry reactor system may be operated at conditions listed above. In another embodiment the catalytic reaction system employs an ebullating bed reactor. Ebullating bed reactor systems are known in the art and an example of an ebullating bed reactor system is described in U.S. Pat. No. 6,436,279.

The effluent stream from the reaction zone contains at least the product polyol(s) and may also contain unreacted water, hydrogen, saccharide, byproducts such as phenolic compounds and glycerol, and intermediates such as depolymerized polysaccharides and lignins Depending upon the catalyst selected and the catalytic reaction system used, the effluent stream may also contain at least a portion of the catalyst system. The effluent stream may contain a portion of the catalyst system that is in the liquid phase, or a portion of the catalyst system that is in the solid phase. In some embodiments it may be advantageous to remove solid phase catalyst components from the effluent stream, either before or after and desired products or by-products are recovered. Solid phase catalyst components may be removed from the effluent stream using one or more techniques such as direct filtration, settling followed by filtration, hydrocyclone, fractionation, centrifugation, the use of flocculants, precipitation, extraction, evaporation, or combinations thereof. In one embodiment, separated catalyst may be recycled to the reaction zone.

Figure 1:
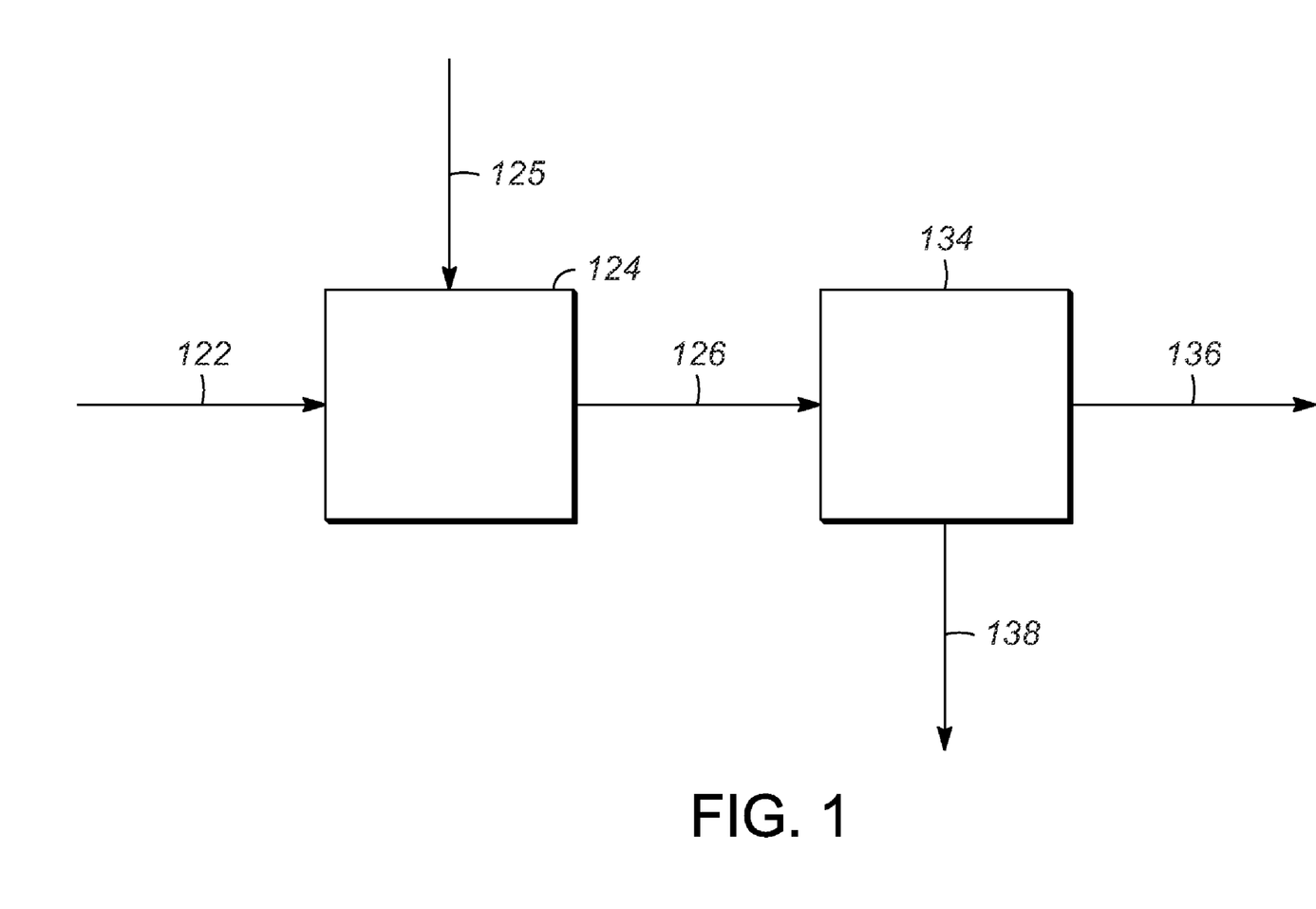
FIG. 1 is a basic diagram of the flow scheme of one embodiment of the invention. Equipment and processing steps not required to understand the invention are not depicted.

Turning to FIG. 1, the catalyst system, water, and feedstock comprising saccharide are conducted via stream 122 to reaction zone 124. The mixture in stream 122 has, for example, a water to feedstock comprising saccharide weight ratio of about 5 and a catalyst system to feedstock comprising saccharide weight ratio of about 0.05. At least hydrogen is conducted via stream 125 to reaction zone 124. Reaction zone 124 is operated, for example, at a temperature of about 250° C. a hydrogen pressure of about 1200 psig, a pH of about 7 and a residence time of about 8 minutes. Prior to introduction into reaction zone 124, the catalyst, water, and feedstock comprising saccharide in stream 122 and the hydrogen in stream 125 are brought to a pressure of about 1800 psig to be at about the same pressure as reaction zone 124. However, only stream 125 comprising at least hydrogen is raised to at least 250° C. to be at a temperature greater than or equal to the temperature in reaction zone 124. The mixture in stream 122 which contains at least the saccharide is temperature controlled to remain at a temperature lower than the decomposition or charring temperature of the saccharide. In reaction zone 124, the saccharide is catalytically converted into at least ethylene glycol or propylene glycol. Reaction zone effluent 126 contains at least the product ethylene glycol or propylene glycol. Reaction zone effluent 126 may also contain alcohols, organic acids, aldehydes, monosaccharides, polysaccharides, phenolic compounds, hydrocarbons, glycerol, depolymerized lignin, and proteins. Reaction zone effluent 126 is conducted to product recovery zone 134 where the desired glycol products are separated and recovered in steam 136. Remaining components of reaction zone effluent 126 are removed from product recovery zone 134 in stream 138.

Figure 2:
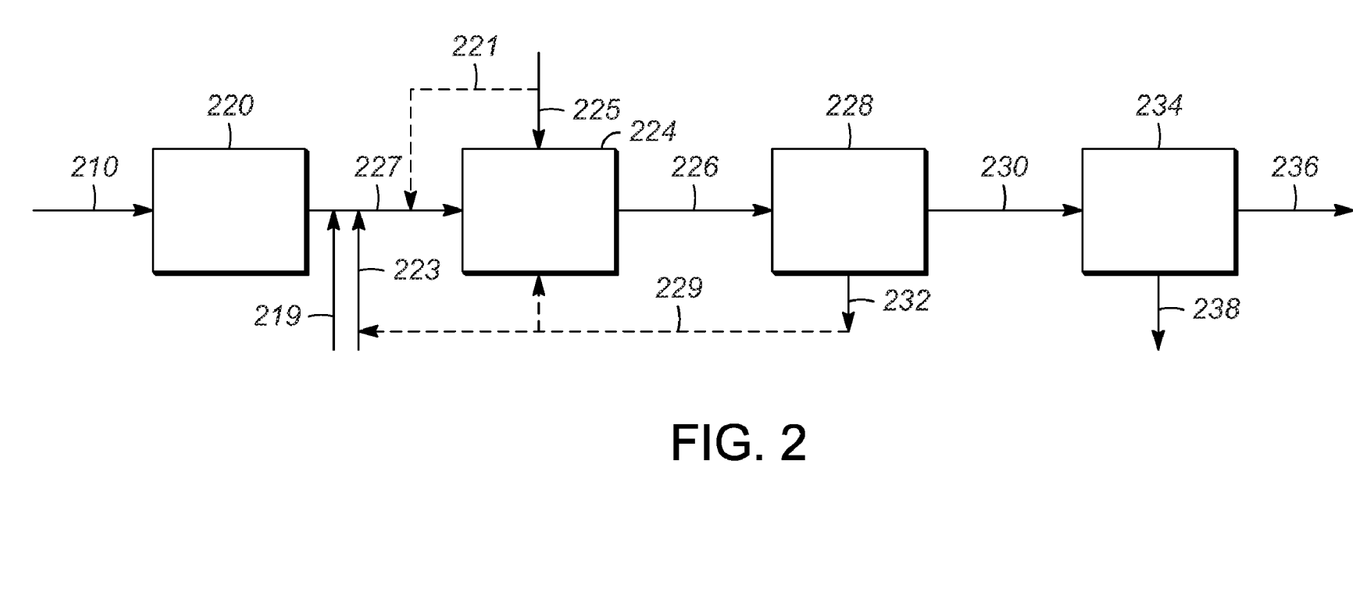
FIG. 2 is a basic diagram of the flow scheme of another embodiment of the invention showing an optional pretreatment zone and an optional supported catalyst component separation zone with optional supported catalyst component recycle. Equipment and processing steps not required to understand the invention are not depicted.

Turning to FIG. 2, water and feedstock comprising polysaccharide 210 is introduced to pretreatment unit 220 where the saccharide is ground to a particle size that is small enough to be pumped as a slurry with the water using conventional equipment. The pretreated feedstock is combined with water in line 219 and catalyst system in line 223 and combined stream 227 is conducted to reaction zone 224. The combined stream 227 has, for example, a water to feedstock comprising saccharide weight ratio of about 20 and a catalyst system to saccharide weight ratio of about 0.1. At least hydrogen is conducted via stream 225 to reaction zone 224. Some hydrogen may be combined with stream 227 prior to reaction zone 224 as shown by optional dotted line 221. Reaction zone 224 is operated, for example, at a temperature of about 280° C. a hydrogen pressure of about 200 psig, a pH of about 7 and a residence time of about 8 minutes. Prior to introduction into reaction zone 224, the catalyst system, water, and pretreated feedstock comprising saccharide in stream 227 and the hydrogen in stream 225 are brought to a pressure of about 1800 psig to be at about the same temperature as reaction zone 224. However, only stream 225 comprising at least hydrogen is raised to at least 250° C. to be at a temperature greater than or equal to the temperature of reaction zone 224. The mixture in stream 227 which contains at least the saccharide is temperature controlled to remain at a temperature lower than the decomposition or charring temperature of the polysaccharide. In reaction zone 224, the saccharide is catalytically converted into at least ethylene glycol or polyethylene glycol.

Reaction zone effluent 226 contains at least the product ethylene glycol or propylene glycol and catalyst. Reaction zone effluent 226 may also contain alcohols, organic acids, aldehydes, monosaccharides, polysaccharides, phenolic compounds, hydrocarbons, glycerol, depolymerized lignin, and proteins. Reaction zone effluent 226 is conducted to optional catalyst system recovery zone 228 where catalyst components are separated from reaction zone effluent 226 and removed in line 232. Catalyst components in line 232 may optionally be recycled to combine with line 223 or to reaction zone 224 as shown by optional dotted line 229. The catalyst component-depleted reaction zone effluent 230 is conducted to product recovery zone 234 where the desired glycol products are separated and recovered in steam 236. Remaining components of effluent 230 are removed from product recovery zone 234 in stream 238.

EXAMPLE

Seventeen experiments were conducted according to the following procedure. 1 gram of saccharide containing feedstock and 100 grams of de-ionized water were added to a 300 ml Parr autoclave reactor. An effective amount of catalyst containing M1 and M2 components were added to the reactor. Details of the feedstocks and type and amount of catalyst are shown in the Table. The autoclave was sealed and purged with $N_2$ followed by $H_2$ and finally pressurized with $H_2$ to about 6 MPa at room temperature. The autoclave was heated up to 245° C. with constant stirring at about 1000 rpm and kept at temperature for 30 minutes. After 30 minutes, the autoclave was cooled down to room temperature and liquid product was recovered by filtration and analyzed using HPLC. Microcrystalline cellulose was obtained from Sigma-Aldrich. Ni on Norit CA-1 catalyst was prepared by impregnating various amounts of Ni using Ni nitrate in water onto activated carbon support Norit-CA1 using incipient wetness technique. The impregnated support was then dried at 40° C. overnight in an oven with nitrogen purge and reduced in H2 at 750° C. for 1 hrs. 5% Pd/C and 5% Pt/C were purchased from Johnson Matthey. Ethylene glycol and propylene glycol yields were measured as mass of ethylene glycol or propylene glycol produced divided by the mass of feedstock used and multiplied by 100.

| No. | Feedstock Type | Feedstock Amount (g) | H2O (g) | Catalyst Component Containing Metal M1 | M1 in Reactor (g) | Catalyst Component Containing Metal M2 | M2 in Reactor (g) | M1/M2 (wt/wt) | (M1 + M2)/Feedstock (wt/wt) | EG Yield (wt %) | PG Yield (wt %) |
|---|---|---|---|---|---|---|---|---|---|---|---|
| 1 | Microcrystalline Cellulose | 1 | 100 | None | 0 | 2% Ni/Norit CA-1 | 0.006 | 0.0 | 0.006 | 2.3 | 1.9 |
| 2 | Microcrystalline Cellulose | 1 | 100 | Tungstic Acid, $WO_3 \cdot xH_2O$ | 0.015 | 2% Ni/Norit CA-1 | 0.006 | 2.5 | 0.021 | 58.0 | 4.3 |
| 3 | Microcrystalline Cellulose | 1 | 100 | Tungsten Oxide, $WO_2$ | 0.008 | 0.6% Ni/Norit CA-1 | 0.0018 | 4.4 | 0.010 | 55.0 | 4.1 |
| 4 | Microcrystalline Cellulose | 1 | 100 | Phosphotungstic Acid $H_3PW_{12}O_{40}$ | 0.015 | 2% Ni/Norit CA-1 | 0.006 | 2.5 | 0.021 | 46.0 | 4.6 |
| 5 | Microcrystalline Cellulose | 1 | 100 | Ammonium Metatungstate $(NH_4)_6(W_{12}O_{40}) \cdot xH_2O$ | 0.015 | 2% Ni/Norit CA-1 | 0.006 | 2.5 | 0.021 | 56.0 | 3.0 |
| 6 | Microcrystalline Cellulose | 1 | 100 | Ammonium Metatungstate $(NH_4)_6(W_{12}O_{40}) \cdot xH_2O$ | 0.03 | 2% Ni/Norit CA-1 | 0.006 | 5.0 | 0.036 | 55.0 | 3.0 |
| 7 | Microcrystalline Cellulose | 1 | 100 | Ammonium Metatungstate $(NH_4)_6(W_{12}O_{40}) \cdot xH_2O$ | 0.06 | 2% Ni/Norit CA-1 | 0.006 | 10.0 | 0.066 | 49.0 | 2.0 |
| 8 | Microcrystalline Cellulose | 1 | 100 | Ammonium Metatungstate $(NH_4)_6(W_{12}O_{40}) \cdot xH_2O$ | 0.12 | 2% Ni/Norit CA-1 | 0.006 | 20.0 | 0.126 | 37.0 | 1.7 |
| 9 | Microcrystalline Cellulose | 1 | 100 | Ammonium Metatungstate $(NH_4)_6(W_{12}O_{40}) \cdot xH_2O$ | 0.015 | 1% Ni/Norit CA-1 | 0.003 | 5.0 | 0.018 | 68.0 | 2.8 |
| 10 | Microcrystalline Cellulose | 1 | 100 | Ammonium Metatungstate $(NH_4)_6(W_{12}O_{40}) \cdot xH_2O$ | 0.008 | 0.6% Ni/Norit CA-1 | 0.0018 | 4.4 | 0.010 | 68.0 | 3.3 |
| 11 | Microcrystalline Cellulose | 1 | 100 | Ammonium Metatungstate $(NH_4)_6(W_{12}O_{40}) \cdot xH_2O$ | 0.008 | 0.2% Ni/CA-1 | 0.0006 | 13.3 | 0.009 | 38.0 | 0.0 |
| 12 | Microcrystalline Cellulose | 1 | 100 | Ammonium Metatungstate $(NH_4)_6(W_{12}O_{40}) \cdot xH_2O$ | 0.06 | 5% Pd/C | 0.015 | 4.0 | 0.075 | 48.0 | 0.0 |
| 13 | Microcrystalline Cellulose | 1 | 100 | Ammonium Metatungstate $(NH_4)_6(W_{12}O_{40}) \cdot xH_2O$ | 0.015 | 5% Pd/C | 0.015 | 1.0 | 0.030 | 42.0 | 1.0 |

-continued

| No. | Feedstock Type | Feedstock Amount (g) | H2O (g) | Catalyst Component Containing Metal M1 | M1 in Reactor (g) | Catalyst Component Containing Metal M2 | M2 in Reactor (g) | M1/M2 (wt/wt) | (M1 + M2)/Feedstock (wt/wt) | EG Yield (wt %) | PG Yield (wt %) |
|---|---|---|---|---|---|---|---|---|---|---|---|
| 14 | Microcrystalline Cellulose | 1 | 100 | Ammonium Metatungstate $(NH_4)_6(W_{12}O_{40}) \cdot xH_2O$ | 0.015 | 5% Pt/C | 0.015 | 1.0 | 0.030 | 17.2 | 2.4 |
| 15 | Bleached Pulp | 1 | 100 | Ammonium Metatungstate $(NH_4)_6(W_{12}O_{40}) \cdot xH_2O$ | 0.008 | 0.6% Ni/Norit CA-1 | 0.0018 | 4.4 | 0.010 | 37.0 | 3.0 |
| 16 | Glucose | 1 | 100 | Ammonium Metatungstate $(NH_4)_6(W_{12}O_{40}) \cdot xH_2O$ | 0.008 | 0.6% Ni/Norit CA-1 | 0.0018 | 4.4 | 0.010 | 29.0 | 6.6 |
| 17 | Glucose | 1 | 100 | Ammonium Metatungstate $(NH_4)_6(W_{12}O_{40}) \cdot xH_2O$ | 0.008 | 0.6% Ni/Norit CA-1 | 0.0018 | 4.4 | 0.010 | 49.0 | 4.1 |

The invention claimed is:

1. A process for generating at least one polyol from a feedstock comprising:
   a) contacting, hydrogen, water, and a feedstock comprising at least one saccharide, with a catalyst system comprising an unsupported component comprising a compound comprising an element selected from the group consisting of IUPAC Groups 4, 5 and 6 of the Periodic Table and having an oxidation state greater than or equal to 2+ wherein the compound of the unsupported component is in a form other than a carbide, nitride or phosphide, and a supported hydrogenation component selected from the group consisting of IUPAC Groups 8, 9, and 10, of the Periodic Table on a solid catalyst support to generate an effluent stream comprising at least one polyol; and
   b) recovering the polyol from the effluent stream.

2. The process of claim 1 wherein the process is operated in a mode selected from the group consisting of batch mode operation and continuous mode operation.

3. The process of claim 1 wherein the contacting occurs in a reaction zone comprising at least a first input stream and a second input stream, the first input stream comprising at least flowing feedstock and the second input stream comprising flowing hydrogen.

4. The process of claim 3 wherein the first input stream is pressurized prior to the reaction zone and the second input stream is pressurized and heated prior to the reaction zone.

5. The process of claim 3 wherein the first input stream is pressurized and heated to a temperature below the decomposition temperature of the saccharide in the feedstock prior to the reaction zone and the second input stream is pressurized and heated prior to the reaction zone.

6. The process of claim 3 wherein the first input stream and the second input stream further comprise water.

7. The process of claim 1 wherein the saccharide of the feedstock is selected from the group consisting of monosaccharides, disaccharides, oligosaccharides, polysaccharides, and combinations thereof.

8. The process of claim 1 wherein the feedstock comprising saccharide is selected from a group consisting of edible saccharides, inedible saccharides, waste materials, recycled materials, and combinations thereof.

9. The process of claim 1 wherein the feedstock comprising saccharide is selected from the group consisting of short rotation forestry, industrial wood waste, forest residue, agricultural residue, energy crops, industrial wastewater, municipal wastewater, paper, cardboard, fabrics, pulp derived from biomass, corn starch, sugarcane, grain, sugar beet, glycogen, molecules comprising the molecular unit structure of $C_m(H_2O)_n$, and combinations thereof.

10. The process of claim 1 wherein the polyol is selected from the group consisting of ethylene glycol and propylene glycol.

11. The process of claim 1 wherein the effluent stream further comprises at least one co-product selected from the group consisting of alcohols, organic acids, aldehydes, monosaccharides, polysaccharides, phenolic compounds, hydrocarbons, glycerol, depolymerized lignin, and proteins.

12. The process of claim 1 further comprising preparing the feedstock comprising saccharide prior to contacting with the catalyst by a technique selected from the group consisting of sizing, drying, grinding, hot water treatment, steam treatment, hydrolysis, pyrolysis, thermal treatment, chemical treatment, biological treatment, catalytic treatment, and combinations thereof.

13. The process of claim 12 wherein the chemical treatment comprises acid catalyzed hydrolysis or base catalyzed hydrolysis, the catalytic treatments comprise depolymerization, hydrogenation, or both, and wherein the biological treatment comprises enzymatic hydrolysis.

14. The process of claim 1 wherein the hydrogen, water, and feedstock is contacted with the catalyst in a reactor having metallurgy comprising a component selected from the group consisting of titanium, zirconium, stainless steel, carbon steel having hydrogen embrittlement resistant coating, carbon steel having corrosion resistant coating.

15. The process of claim 1 wherein the hydrogen, water, and feedstock is contacted with the catalyst in a system selected from the group consisting of an ebullating catalyst bed system, an immobilized catalyst system having catalyst channels, an augured reaction system, a fluidized bed reaction system, a mechanically mixed reaction system, a slurry reactor system, and combinations thereof.

16. The process of claim 1 wherein the hydrogen, water, and feedstock are contacted with the catalyst system in a slurry reactor system operated at a temperature ranging from about 100° C. to about 350° C. and a hydrogen pressure greater than about 150 psig.

17. The process of claim 1 wherein the hydrogen, water, and feedstock are contacted with the catalyst in a reaction zone operated at conditions sufficient to maintain at least a portion of the water in the liquid phase.

18. The process of claim 1 wherein the hydrogen, water, and feedstock are continuously contacted with the catalyst system in a slurry reactor system operated at a water to feedstock weight ratio ranging from about 1 to about 100, a catalyst to feedstock weight ratio of greater than about 0.005, a pH of less than about 10 and a residence time of greater than 5 minutes.

19. The process of claim 1 wherein the effluent stream further comprises catalyst, said process further comprising separating catalyst from the effluent stream using a technique selected from the group consisting of direct filtration, settling followed by filtration, hydrocyclone, fractionation, centrifugation, the use of flocculants, precipitation, liquid extraction, adsorption, evaporation, and combinations thereof.

20. The process of claim 19 further comprising recycling the separated catalyst to the reactor.

* * * * *